United States Patent
Payne et al.

(10) Patent No.: US 8,147,707 B2
(45) Date of Patent: Apr. 3, 2012

(54) FIBRES TREATED WITH ANTIMICROBIAL AGENTS

(75) Inventors: John David Payne, Rossendale (GB); John Edward Yates, Rochdale (GB)

(73) Assignee: Arch UK Biocides Limited, Manchester (GB)

( * ) Notice: Subject to any disclaimer, the term of this patent is extended or adjusted under 35 U.S.C. 154(b) by 521 days.

(21) Appl. No.: 10/580,802

(22) PCT Filed: Nov. 10, 2004

(86) PCT No.: PCT/GB2004/004738
§ 371 (c)(1),
(2), (4) Date: Apr. 16, 2007

(87) PCT Pub. No.: WO2005/054566
PCT Pub. Date: Jun. 16, 2005

(65) Prior Publication Data
US 2007/0271707 A1    Nov. 29, 2007

(30) Foreign Application Priority Data
Nov. 28, 2003  (GB) .................................. 0327693.8

(51) Int. Cl.
*D06M 13/325* (2006.01)
*D06M 11/155* (2006.01)
(52) U.S. Cl. .................... 252/8.61; 252/8.84; 8/115.65; 8/181; 8/195; 442/59; 442/123

(58) Field of Classification Search ......... 8/181, 115.65, 8/120, 195; 252/8.6, 8.9, 8.61, 8.84; 442/59, 442/123
See application file for complete search history.

(56) References Cited

U.S. PATENT DOCUMENTS

| 3,082,118 | A | | 3/1963 | Shaw et al. | |
|---|---|---|---|---|---|
| 4,396,391 | A | * | 8/1983 | North | ................. 8/181 |
| 5,352,372 | A | * | 10/1994 | North | ................. 442/59 |
| 5,700,742 | A | * | 12/1997 | Payne | ............. 442/123 |
| 2001/0021616 | A1 | | 9/2001 | Bullock et al. | |
| 2003/0096993 | A1 | * | 5/2003 | Hayoz | ............ 544/215 |

FOREIGN PATENT DOCUMENTS

| JP | 02-114467 | 4/1990 |
|---|---|---|
| JP | 04-011076 | 1/1992 |
| WO | 95/12021 | 5/1995 |

* cited by examiner

*Primary Examiner* — Lorna M Douyon
*Assistant Examiner* — Amina Khan
(74) *Attorney, Agent, or Firm* — Dale L. Carlson; Wanli Wu; Wiggin and Dana LLP

(57) ABSTRACT

A composition for inhibiting the growth of microorganisms on non-cellulosic fibers having a moisture regain of $\leq 5\%$, comprising;
 i) 1 to 50 wt % of at least a self-crosslinkable resin;
 ii) 0.25 to 20 wt % of at least a catalyst;
 iii) 0.1 to 4 wt % of at least an antimicrobial active agent, reactive with the resin;
 iv) 98.65 to 26 wt % of water;
wherein i)+ii)+iii)+iv)=100%.

16 Claims, No Drawings

FIBRES TREATED WITH ANTIMICROBIAL AGENTS

The present invention relates to a composition for inhibiting the growth of microorganisms on non-cellulosic fibres comprising a self-crosslinkable resin, a catalyst and an antimicrobial active agent that is reactive with the self-crosslinkable resin; a method for treating non-cellulosic fibres with the composition and non-cellulosic fibres treated with the composition.

The use of antimicrobial active agents for treating cellulosic fibres is well known. During the processing of cellulosic fibres such as cotton and viscose, oxidation of cellulose takes place with the formation of carboxylic acid groups. Cationic antimicrobial active agents such as poly(hexamethylene biguanide) can be attached to cellulosic fibres by means of ionic bonding between the cationic antimicrobial active agents and anionic carboxylic acid groups.

JP 5-226185 discloses a process for fixing a polyhexamethylene biguanide type compound to a textile material by crosslinking the antimicrobial active agent to textiles having hydroxy functionality with a crosslinking agent.

There is however a need for treating non-cellulosic fibres with antimicrobial active agents. Non-cellulosic fibres include but are not limited to protein based fibres of animal origin such as wool, silk, fur, leather and hair; synthetic fibres such as fibres based on polyester, aliphatic polyamide (e.g. Nylon), aromatic polyamide (e.g. Aramid), polypropylene, polyethylene, poly(vinyl chloride), fluorocarbon (e.g. poly(tetrafluoroethylene) PTFE) and polyurethane (e.g. Lycra™, Spandex™); fibres of mineral origin such as glass, carbon, ceramics and metal; and fibres of plant origin where any carboxylic acid groups have been chemically reacted so as to be unreactive such as cellulose acetate.

Antimicrobial active agents may be applied to non-cellulosic fibres by padding but there is no interaction between the non-cellulosic fibre and the antimicrobial active agent and consequently there is no durability to laundering or rinsing. Furthermore if antimicrobial active agents are used that may have adverse dermal effects, then such a system would not be feasible in applications requiring skin contact.

We have found that it is possible to immobilise antimicrobial active agents onto non-cellulosic fibres by means of self-crosslinkable resins without the need for ionic bonding or covalent crosslinking between the non-cellulosic fibre and the antimicrobial active agent.

In particular we have found that it is possible to immobilise antimicrobial active agents onto non-cellulosic fibres with very few or no active hydrogens. It is difficult to measure the concentration of active hydrogens on a fibre however a closely related property is the degree of hydrophilicity of a fibre. The hydrophilicity of fibres may be defined using a number of parameters including the acid value of the fibre and or the moisture regain of the fibre.

The measurement of acid values is described in "Comprehensive Cellulose Chemistry" D. Klemm, B. Philipp, T. Heinze, U. Heinze and W. Wagenknecht, Volume 1, Fundamentals and Analytical Methods, Wiley-VCH, 1998, ISBN 3-527-29413-9. The technique used for the measurement of acid values of fibres is described below.

Moisture regain is the quantity of water picked up by a totally dry fibre and is detailed in ASTM D2495 and D1909. The technique used for the measurement of moisture regain is described below.

According to the present invention there is provided a composition for inhibiting the growth of microorganisms on non-cellulosic fibres having a moisture regain of $\leq 5\%$ comprising:
  i) 1 to 50 wt % of at least a self-crosslinkable resin;
  ii) 0.25 to 20 wt % of at least a catalyst;
  iii) 0.1 to 4.0 wt % of at least an antimicrobial active agent, reactive with the resin;
  iv) 98.65 to 26 wt % of water;
wherein i)+ii)+iii)+iv)=100%.

Preferably the non-cellulosic fibres have a moisture regain $\leq 4.5\%$, more preferably $\leq 4.0\%$, most preferably $\leq 3.0\%$, especially $\leq 2.0\%$ and most especially $\leq 1.5\%$.

According to an alternative embodiment of the invention there is also provided a composition for inhibiting the growth of microorganisms on non-cellulosic fibres having an acid value of $\leq 5$ mmol/kg comprising:
  i) 1 to 50 wt % of at least a self-crosslinkable resin;
  ii) 0.25 to 20 wt % of at least a catalyst;
  iii) 0.1 to 4.0 wt % of at least an antimicrobial active agent, reactive with the resin;
  iv) 98.65 to 26 wt % of water Preferably the non-cellulosic fibres have an acid value $\leq 4$ mmol/kg, more preferably $\leq 3$ mmol/kg and most preferably $\leq 2$ mmol/kg.

Preferred non-cellulosic fibres are synthetic fibres. Most preferably non-cellulosic fibres include polyester, polyamide (Nylon), polypropylene, polyurethane (Lycra™, Spandex™) and cellulose acetate.

Preferably the composition comprises 1 to 40 wt %, more preferably 2 to 20 wt % and most preferably 3 to 12 wt % of at least a self-crosslinkable resin.

Preferably the composition comprises 0.25 to 10 wt %, more preferably 0.5 to 5 wt % and most preferably 0.75 to 3 wt % of at least a catalyst.

Preferably the composition comprises 0.2 to 4.0 wt %, more preferably 0.2 to 3.0 wt % and, most preferably 0.4 to 1.6 wt % of at least an antimicrobial active agent reactive with resin.

Preferably the composition comprises 60 to 98 wt % of water, more preferably 75 to 97 wt % and most preferably 80 to 95 wt % of water.

Preferably the weight ratio of self-crosslinkable resin to antimicrobial active agent reactive with the self-crosslinkable resin is in the range of from 1:1 to 20:1 more preferably in the range of from 1:1 to 15:1 and most preferably in the range of from 2:1 to 10:1.

The self-crosslinkable resin of the invention may be based on formaldehyde condensates with urea or melamine which may be additionally modified to reduce undesirable free formaldehyde levels. (Free formaldehyde gives rise to unpleasant odours and may cause skin reactions). Additional formaldehyde condensates include ethylene urea, benzoguanamine thiourea and acetoguanamine.

Suitable self-crosslinkable resins may be described as amino resins, more preferably etherified amino resins and most preferably comprise urea-formaldehyde and melamine formaldehyde resins, and in particular methylated and butylated urea-formaldehyde and melamine-formaldehyde resins.

Self-crosslinkable resins that have ethylene incorporated and that release lower levels of formaldehyde are preferred and include dimethyloldihydroxyethylene urea [DMDHEU] and dihydroxydimethylene urea [DHDMEU]. The remaining hydroxyl groups of such self-crosslinkable resins may be further etherified with butyl or methyl groups to still further lower free formaldehyde levels and such self-crosslinkable resins are often known as formaldehyde-free resins.

Preferably urea-formaldehyde resins are utilised due to having a lower crosslinkable density resulting in improved handling.

Preferably very low and most preferably formaldehyde-free resins are utilised.

Self-crosslinkable resins for use in accordance with the present invention (but not limited there to) are available from commercial suppliers, under the following trade names as shown in Table 1 below:

TABLE 1

| Trade name of self-crosslinkable resin | Chemical type | Commercial Supplier |
|---|---|---|
| VALREZ | DMDHEU resins with low formaldehyde | APS Chemicals |
| AIROREZ | Low to zero formaldehyde melamine and urea resins | Airedale Chemical Co Ltd |
| FABRISET | DMDHEU resins with low formaldehyde | Alphachem Specialties Ltd |
| AVCO-REZ | DMDHEU resins with low formaldehyde | Avco Chemicals Ltd |
| BAYPRET | Etherified melamine form | Bayer AG |
| ACROFIX | Etherified melamine form | Bayer AG |
| AC119 TO176 BEETAFIN L 9009-9801 | Methylated DMDHEU | BIP Ltd |
| BEETLE RESIN PT | Methylolmelamine form | |
| ELASTOFIX | DMDHEU resins with low formaldehyde | Boehme KG Chem Fab GmbH + Co |
| REACEL | UF, MF, glyoxal and DMEU resins | Giovanni Bozzetto Spa |
| REAPRET | | |
| APOMUL | DMDHEU resins, melamine and urea-formaldehyde resins | Brookstone Chemicals Ltd |
| FIXAPRET | HMDEU, HMU | BASF plc |
| KAURIT | MMM | |
| HELIZARIN | MMM polycondensate | |
| KNITTEX | Modified DMDHEU | Ciba Specialty Chemicals Inc |
| LYOFIX | Alkyl modified | |
| ALCOPRINT | Melamine/form | |
| ARKOFIX | Modified DMDHEU low to zero formaldehyde | Clariant International AG |
| CASSURIT | | |
| REAKNITT | Etherified DMDHEU | R. Beitlich GmbH |
| STABITEX | Methoxymethyl melamine | Cognis Deutschland GmbH |
| PERMAFRESH | DMDHEU, glyoxal, melamine and urea-formaldehyde resins | Contract Chemicals Ltd |
| ALBUTEX | Melamine and urea-formaldehyde resins | BF Goodrich Corporation Noveon Inc. |
| HYCAR | | |
| RUCON | DMDHEU, HMU MMM | Rudolf GmbH and Co KG |
| SARALINK | Low formaldehyde resin | Sarex Overseas |
| RESIN | Methyloldihydroxy ethylene urea MF | Texchem Ltd Dyestuffs |
| TEXFIN | | |
| TEXCHEM | | |
| PERMUTEX | | |
| TC-REAKTANT | Low formaldehyde resin | Textilcolor AF |
| SERIREZ | MF, UF, methylated UF resins | Yorkshire Chemicals plc |
| EDUNINE | Low formaldehyde resin | Uniquema |
| DUPRANIN | Etherified dimethylol glyoxal | Thor Specialties UK Ltd |
| QUECODUR | | |
| DRYWEAR | Low formaldehyde resin | Rotta GmbH |
| NOVAROL | Melamine, glyoxal resins | Novaria Snc |

Key: UF = urea/formaldehyde, MF = melamine/formaldehyde, DMEU = dimethylol ethylene urea, HMDEU = hydroxymethyl diethylene urea, MMM = methylated methylol melamine To initiate the self-crosslinking reaction of the resin a catalyst is required. Suitable catalysts include metal chloride catalysts such as magnesium chloride and ammonium chloride; ammonium sulphate; ammonium salts of strong acids such as formic acid, boric acid, phosphoric acid, oxalic acid and amine hydrochloride catalysts such as polyhexamethylene biguanide [PHMB] hydrochloride, where the chloride ions act as a catalyst. However it is preferred to have an added catalyst (that is not PHMB). If PHMB is used as a catalyst then amount used for component ii) and iii) are still as described above. Preferably the catalyst is selected from the group consisting of $MgCl_2$; ammonium chloride; ammonium sulphate; ammonium salts of formic acid, boric acid, phosphoric acid, oxalic acid; and or mixtures thereof.

Catalysts may contain additives such as citric acid. The function of additional additives may be to increase the cure rate, reduce yellowing and or mop up any released formaldehyde.

Antimicrobial active agents are used to inhibit the growth of microorganisms such as bacteria, fungi, viruses, algae, yeasts and protozoa. Suitable antimicrobial active agents for use in the present invention are agents with reactive hyroxyl or amine groups that are covalently reactive with the self-crosslinkable resin. Examples include but are not limited to quaternary ammonium salts, biguanide and monoguanide type antimicrobial active agents, phenolics, alcohols and 2-bromo-2-nitropropane-1,3-diol. Preferably the antimicrobial active agent is selected from the group consisting of quaternary ammonium salts, biguanides, monoguanides, and or mixtures thereof.

Polyhexamethylene biguanide hydrochloride may therefore be used in both capacities, i.e. the chloride ions as a catalyst and the polyhexamethylene biguanide part as an antimicrobial active agent.

Preferably the antimicrobial active agents are selected from biguanides and monoguanides.

Preferably the biguanide comprises at least two biguanide units of Formula (1):

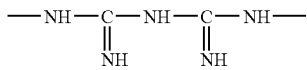
Formula (1)

linked by a bridging group which contains at least one methylene group. The bridging group preferably includes a polymethylene chain, optionally incorporating or substituted by one or more hetero atoms such as oxygen, sulphur or nitrogen. The bridging group may include one or more cyclic moieties which may be saturated or unsaturated. Preferably, the bridging group is such that there are at least three, and especially at least four, carbon atoms directly interposed between two adjacent biguanide units of Formula (1). Preferably, there are not greater than ten and especially not greater than eight carbon atoms interposed between two adjacent biguanide units of Formula (1).

The biguanide may be terminated by any suitable group, such as a hydrocarbyl group, a substituted hydrocarbyl group, an amine group or a cyanoguanidine group of the Formula (2):

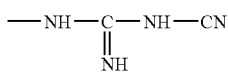
Formula (2)

When the terminating group is hydrocarbyl, it is preferably alkyl, cycloalkyl, aryl or aralkyl. When the hydrocarbyl group is alkyl it may be linear or branched but is preferably linear. Preferred alkyl groups include $C_{1-8}$-alkyl. Examples of preferred alkyl groups include for example methyl, ethyl, n-propyl, isopropyl, n-pentyl, n-butyl, isobutyl, tert-butyl and n-octyl.

When the hydrocarbyl group is cycloalkyl, it is preferably cyclopropyl, cyclopentyl or cyclohexyl. When the hydrocarbyl group is aralkyl, it preferably contains from 1 to 6, more preferably 1 or 2 carbon atoms in the alkylene group attaching the aryl group to the biguanide. Preferred aralkyl groups include benzyl and 2-phenylethyl groups.

Preferred aryl groups include phenyl groups. When the terminating group is substituted hydrocarbyl, the substituent may be any substituent that does not exhibit undesirable adverse effects on the microbiological properties of the polymeric biguanide. Examples of such substituents are aryloxy, alkoxy, acyl, acyloxy, halogen and nitrile.

When the biguanide contains two biguanide groups of Formula (1) the biguanide is a bisbiguanide. The two biguanide groups are preferably linked through a polymethylene group, especially a hexamethylene group.

The terminating groups in such bisbiguanides are preferably $C_{1-10}$-alkyl which may be linear or branched and optionally substituted aryl, especially optionally substituted phenyl. Examples of such terminating groups are 2-ethylhexyl and 4-chlorophenyl. Specific examples of such bisbiguanides are compounds represented by Formula (3) and (4) in the free base form:

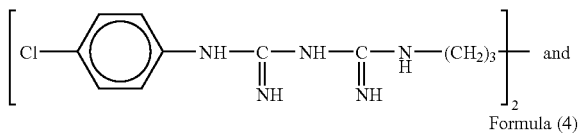
Formula (3)

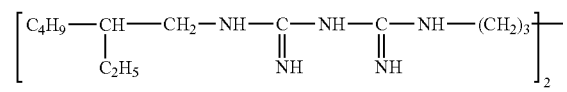
Formula (4)

The biguanide preferably contains more than two biguanide units of Formula (1) and is preferably a linear polymeric biguanide which has a recurring polymeric chain represented by Formula (5) or a salt thereof:

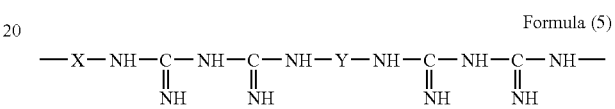
Formula (5)

wherein X and Y represent bridging groups which may be the same or different and in which together the total of the number of carbon atoms directly interposed between the pairs of nitrogen atoms linked by X plus the number of carbon atoms directly interposed between the pairs of nitrogen atoms linked by Y is more than 9 and less than 17.

The bridging groups X and Y preferably consists of polymethylene chains, optionally interrupted by hetero atoms, for example, oxygen, sulphur or nitrogen. X and Y may also incorporate moieties which may be saturated or unsaturated, in which case the number of carbon atoms directly interposed between the pairs of nitrogen atoms linked by X and Y is taken as including that segment of the cyclic group, or groups, which is the shortest. Thus, the number of carbon atoms directly interposed between the nitrogen atoms in the group

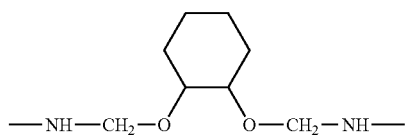

is 4 and not 8.

The linear polymeric biguanides having a recurring polymer unit of Formula (5) are typically obtained as mixtures of polymers in which the polymer chains are of different lengths. Preferably, the number of individual biguanide units of Formulae (5a) and (5b) is together from 3 to about 80.

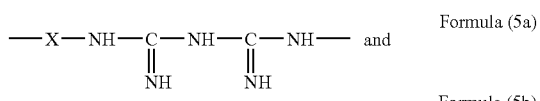
Formula (5a)

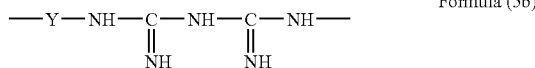
Formula (5b)

The preferred linear polymeric biguanide is a mixture of polymer chains in which X and Y are identical and the individual polymer chains, excluding the terminating groups, are of the Formula (6) or a salt thereof:

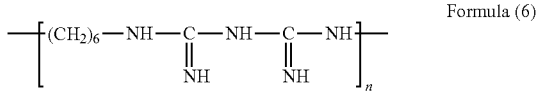

Formula (6)

wherein n is from 4 to 20 and especially from 4 to 18. It is especially preferred that the average value of n is about 16. Preferably, the average molecular weight of the polymer in the free base form is from 1100 to 4000.

The linear polymeric biguanides may be prepared by the reaction of a bisdicyandiamide having the Formula (7):

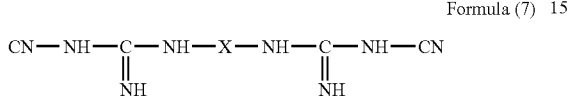

Formula (7)

with a diamine $H_2N$—Y—$NH_2$, wherein X and Y have the meanings defined above, or by the reaction between a diamine salt of dicyanamide having the Formula (8):

Formula (8)

with a diamine $H_2N$—Y—$NH_2$, wherein X and Y have the meanings defined above. These methods of preparation are described in GB patent numbers 702,268 and 1,152,243 respectively, and any of the polymeric biguanides described therein may be used in the present invention. As noted hereinbefore, the polymer chains of the linear polymeric biguanides may be terminated either by an amino group or by a cyanoguanidine group of Formula (9):

Formula (9)

This cyanoguanidine group can hydrolyse during preparation of the linear polymeric biguanide yielding a guanidine end group. The terminating groups may be the same or different on each polymer chain. A small proportion of a primary amine R—$NH_2$, wherein R represents an alkyl group containing from 1 to 18 carbon atoms, may be included with the diamine $H_2N$—Y—$NH_2$ in the preparation of polymeric biguanides as described above. The primary amine acts as a chain-terminating agent and consequently one or both ends of the polymeric biguanide polymer chains may be terminated by an —NHR group. These —NHR chain-terminated polymeric biguanides may also be used. The polymeric biguanides readily form salts with both inorganic and organic acids. Preferred salts of the polymeric biguanide are water-soluble. When the polymeric biguanide is represented by a compound of Formula (3) in the free base form, a preferred water soluble salt is the digluconate. This is commercially available from Avecia Limited under the trademark Vantocil™ CHG. When the polymeric biguanide is a mixture of linear polymers represented by Formula (6) in the free base form, the preferred salt is the hydrochloride.

It is especially preferred that the polymeric biguanide used in accordance with the present invention is a mixture of linear polymers, the individual polymer chains of which, excluding the terminating groups, are represented by Formula (6) in the hydrochloride salt form. This poly(hexamethylenebiguanide) compound is commercially available from Avecia Limited under the trademark Reputex™ 20.

Poly($C_{2-18}$-hydrocarbyl mono guanidine)s ("PMG") are distinguished from PHMB by the fact that they contain mono guanidine groups whereas PHMB contains no mono guanidine groups and instead contains biguanide groups of formula —NHC═(NH)NHC(═NH)NH—.

The PMG preferably comprises a plurality of groups of Formula (10) and/or groups of Formula (11) or salts thereof:

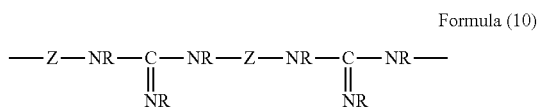

Formula (10)

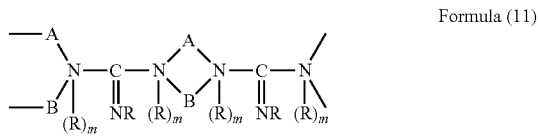

Formula (11)

wherein:
each m independently is 0 or 1;
each Z independently is a $C_{2-18}$-hydrocarbyl group;
A and B are hydrocarbyl groups which together comprise a total of 3 to 18 carbon atoms;
each R independently is hydrogen, optionally substituted alkyl or optionally substituted alkoxy.

Preferably each m is 0.

The hydrocarbyl groups in the PMG and represented by Z, A and B are optionally interrupted by one or more hetero atoms or groups and optionally carry one or more substituents other than hydrogen. Preferred interrupting atoms and groups are —O—, —S—, —NH—, —C(═O)— and phenylene. Preferred optional substituents are hydroxy; $C_{1-4}$-alkoxy; halo, especially chloro or bromo; nitro; amino; substituted amino; and acid groups, especially carboxy, sulpho and phosphato.

Preferably the hydrocarbyl groups in the PMG and represented by Z are $C_{2-18}$-alkylene (more preferably $C_{4-16}$-alkylene, especially $C_{6-12}$-alkylene, more especially $C_6$-alkylene); $C_{3-12}$-arylene, more preferably $C_{6-10}$-arylene, especially phenylene or naphthylene; $C_{7-12}$-arakylene (more preferably $C_{7-11}$-arylene, especially benzylene or xylylene); or a combination thereof, optionally interrupted by one or more —O—, —S—, —NH— or —C(═O)— groups.

Preferably the hydrocarbyl groups represented by A and B are each independently $C_{2-6}$-alkylene, optionally interrupted by one or more —O—, —S—, —NH— or —C(═O)— groups, with the proviso that A and B comprise a total of 3 to 12 carbon atoms, preferably 3 to 6 carbon atoms, more preferably 3 or 4 carbon atoms. In an especially preferred embodiment one of A or B is —$CH_2$— or —$(CH_2)_2$— and the other is —$(CH_2)_2$—, more especially both A and B are —$(CH_2)_2$—.

Examples of preferred-hydrocarbyl groups represented by Z include —$CH_2C_8H_4CH_2$—, —$CH_2OC_6H_4OCH_2$—, —$CH_2OC_6H_{10}OCH_2$—, —$(CH_2)_3O(CH_2)_3$— and —$(CH_2)_2S(CH_2)_2$—.

Examples of particularly preferred-hydrocarbyl groups represented by Z include —$(CH_2)_6$—, —$(CH_2)_8$—, —$(CH_2)_{12}$—, —$CH_2CH(—CH_3)(CH_2)_4CH_3$, 1,4-, 2,3- and 1,3-butylene, 2,5-hexylene, 2,7-heptylene and 3-methyl-1,6-hexylene.

It is preferred that all groups represented by Z are the same and are $C_{4-16}$-alkylene, more preferably $C_{4-12}$-alkylene, especially $C_{4-8}$-alkylene, more especially 1,6-hexylene.

Preferably each R independently is H, $C_{1-4}$-alkyl, $C_{1-4}$-alkoxy or $C_{1-4}$-alkoxy-OH, more preferably H or methyl, especially H.

Preferably the PMG consists essentially of groups of Formula (10).

Preferably all groups represented by R are the same.

More preferably all groups represented by R are H.

The nature of the terminating groups on the PMG is not believed to be critical. Preferred terminating groups on the PMG are amino and guanidino.

In view of the foregoing preferences the PMG preferably comprises one or more groups of Formula (12) or salts thereof:

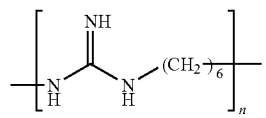

Formula (12)

wherein:
n is 2 to 50, preferably 3 to 25.

Preferably the PMG is in the form of a salt. Preferred salts are those with organic or inorganic acids, especially water-soluble salts, for example the gluconate, acetate or phosphate salt.

The PMGs may be prepared by the reaction of guanidine hydrochloride with a diamine, for example of the formula $H_2N-Y-NH_2$, $HN(-A-)$ $(-B-)NH$ or with a mixture of such diamines, wherein Z, A and B are as defined above.

It is to be understood that the PMG may also contain small amounts of repeating units other than repeat units of Formula (10) and (11). However it is preferred that the PMG consist essentially of or consists of repeat units of Formula (10) and/or (11) and terminating groups.

Examples include polyhexamethylene monoguanide such as SKAN B™ available from SK Corp, Korea and poly(oxyethylene)guanide hydrochloride such as Akacid™ available from POC, Austria.

A suitable example of a non-polymeric monoguanide includes n-docylguanide hydrochloride.

The composition may be diluted with water, aqueous solvents, organic solvents and or mixtures thereof before application to the non-cellulosic fibres. Preferably the composition may be diluted with water and or alcohols, in particular glycols, which are water-miscible and have a low volatility and more preferably the composition may be diluted with water.

Optionally the composition of the present invention may also include dyes; deodorant; UV-absorbents; non-crosslinkable resins; softeners; wicking agents; water repelling agents; antistatic agents; stain repelling agents; lubricants such as polytetrafluoroethylene (PTFE) and other additives well known to the person skilled in the art in the textile industry.

In a second embodiment of the present invention there is provided a method for inhibiting the growth of microorganisms on non-cellulosic fibres having a moisture regain of $\leq 5\%$ and or acid value of $\leq 5$ mmol/kg comprising stages:

A) contacting the fibres with a composition comprising:
  i) 1 to 50 wt % of at least a self-crosslinkable resin;
  ii) 0.25 to 20 wt % of at least a catalyst;
  iii) 0.1 to 4 wt % of at least an antimicrobial active agent, reactive with the resin;
  iv) 98.65 to 26 wt % of water;
  wherein i)+ii)+iii)+iv)=100%;

B) optionally drying the fibres contacted with the composition; and

C) curing the fibres contacted with the composition to effect crosslinking of the resin.

The compositions according to the first aspect of the invention may be applied to the non-cellulosic fibres (or yarns or fabrics made thereof) by any of the wet finishing techniques known in the art for example spraying, dipping or padding processes. Padding involves application of a composition to materials either by passing material through a bath and then through squeeze rollers or by simply passing through squeeze rollers, the lower one of which is partially or wholly immersed in the composition. Such techniques can be used in a single-dip, single squeeze operation or can be more complicated (for example, double dip, double-nip padding, or multiple dip, single nip, etc). For woven material such as bedding and towelling the composition is preferably applied by padding the compositions onto the rolls of the woven material. A further wet application technique involves the use of a spray or dribble bar to apply the composition to a moving bed of loose fibres or a composite non-woven material.

After contacting the fibres with composition, excess liquid is removed by for example squeezing followed by a curing state to cause the self-crosslinkable, resin to cross-link and to effect reaction between the antimicrobial active agent and the self-crosslinkable resin. Preferably the antimicrobial active agent is covalently reactive with the resin. Preferably the curing stage is carried out at temperatures in the range of from 100 to 180° C., more preferably in the range of from 140 to 180° C. and most preferably in the range of from 140 to 160° C.

Obviously the exact cure time and temperature depend on the exact device used, however the cure time is preferably in the range of from 30 seconds to 5 minutes.

According to a third aspect of the invention there are provided non-cellulosic fibres having a moisture regain of $\leq 5\%$ and or an acid value of $\leq 5$ mmol/kg carrying a composition comprising:
  (a) 1 to 10 wt % by weight of the non-cellulosic fibres of at least a self-crosslinkable resin; and
  (b) 0.1 to 1 wt % by weight of the non-cellulosic fibres of at least an antimicrobial active agent reacted with the resin.

According to a fourth aspect of the present invention there are provided non-cellulosic fibres having a moisture regain of $\leq 5\%$ and or an acid value of $\leq 5$ mmol/kg treated with a composition according to the first aspect of the present invention.

According to a fifth aspect of the present invention there is provided the use of a composition according to the first aspect of the present invention in the treatment of non-cellulosic fibres having a moisture regain of $\leq 5\%$ and or an acid value of $\leq 5$ mmol/kg.

The invention is further illustrated by the following examples wherein all references are to parts by weight, unless otherwise stated.

Test Methods

Moisture Regain

The standard test method for moisture regain for cotton and cotton blends is described in ASTM D2495, and is used for the non-cellulosic fibres described herein. Moisture regain is defined as the amount of water in a material specimen determined under prescribed conditions and expressed as a percentage of the mass of the water-free material specimen. In essence the fibre specimens are weighed, dried in an oven until a constant weight is reached and then the difference between the original mass and the oven-dry mass is calculated as a percentage.

Typical commercial moisture regain values are given in ASTM D1909 and are: wool (13.6%), silk (11%), Rayon (11%), cotton (8.5%), nylon (polyamide) (4.5%), polyester (0.4%), acrylic (1.5%), polyurethane (Spandex) (1.3%), polypropylene (olefin) (0.0%), polyvinyl chloride (Vinyon) (0.0%) and fluorocarbon (Teflon) (0.0%).

In the examples below a polyester fibre with a moisture regain of 0.4% was used.

Acid Values

The acid value of a fibre was determined by the uptake of PHMB.

8 g of the fibre to be tested was immersed in 120 g of an 80 ppm PHMB solution (in distilled water) and was stirred at 40° C. for one hour. This is known as exhaustion.

The ratio of solution to fibre is known as the liquor ratio and in this method the liquor ratio is 120/8=15.

The UV/visible spectrum of PHMB solution was measured at 235 nm before and after exhaustion of the fibre. From a calibration graph the concentration of PHMB was calculated before and after exhaustion.

The acid value of the fibre is given by equation 1:

$$\text{Acid value (mmol/kg)} = \frac{\text{difference in } PHMB \text{ concentration}(ppm \times \text{liquor ratio})}{\text{molecular weight of } PHMB} \quad (\text{Eq. 1})$$

Typical acid values are cotton (30 mmol/kg), viscose (60 mmol/kg), nylon (1.6 mmol/kg, polyester (red, knitted 0.91 mmol/kg), polyester (blue, woven 0.57 mmol/kg).

In the examples below a polyester fibre with an acid value of 1.07 mmol/kg was used.

Levels of Antimicrobial Active Agents

Determination of levels of antimicrobial active agents with cationic groups, such as PHMB on treated fibres was carried out by staining with Eosin Y.

Eosin Y Test Solution

A stock solution of Eosin Y was prepared by dissolving Eosin Y [15 g of 80% 2',4',5',7'-tetrabromofluorescein disodium salt indicator grade available from Aldrich Chemical Co.] in distilled water [1500 cm$^3$] and then further diluted to 2500 cm$^3$ with distilled water.

200 cm$^3$ of the stock solution of Eosin Y prepared above was mixed with distilled water [1500 cm$^3$] and sodium citrate [100 g] was added. After complete dissolution of the sodium citrate the solution was further diluted to 2000 cm$^3$ with distilled water to give a Eosin Y test solution.

Staining Procedure

A sample of the fibre to be tested (about 0.2 g) was weighed accurately, placed in a 30 cm$^3$ vial and 100 times the weight (of the fibre) of Eosin Y test solution was added, before sealing the vial and placing the vial on rollers at ambient temperature for 20 minutes.

The fibre sample was removed, rinsed in cold water and then placed in about 800 cm$^3$ of warm water and stirred for 5 minutes. This rinsing step was repeated a further three times before the fibre samples were dried at 50° C.

Estimation of Treatment Levels

Measurement of the reflectance spectrum of stained fibre samples were carried out using an X-Rite SP62 spectrometer. Alternatively a direct visual comparison of the stained fibre sample with a range of stained reference samples may also be used to give an acceptable estimate of the treatment level.

Assessment of Antimicrobial Activity

The AATCC 100 Test Method (1998) is a quantitative test for measuring the bacterial population on for example a sample of textile material made up of non-cellulosic fibres, and hence determining the antimicrobial efficacy. The procedure may be summarised as follows. A culture of *Klebsiella pneumoniae* shaken overnight in nutrient broth was diluted to approximately $1 \times 10^5$ cells/cm$^3$ in 5% sterile physiological saline solution. Two samples (each 0.5 g) were taken from each piece of treated cloth, and inoculated with 1 cm$^3$ of the suspension of *Klebsiella pneumoniae*. After inoculation, one sample of the cloth was immediately neutralised with 100 cm$^3$ of neutraliser solution (CEN standard neutraliser), and shaken vigorously for 60 seconds. The surviving cells were counted by a serial dilution pour plate technique on nutrient agar plates, using saline solution as diluent. The other inoculated sample was incubated at 37° C. for 24 hours. The neutralising and counting technique was then carried out as described above. Further details of this technique can be found in AATCC Technical Manual, published by the American Association of Textile Chemists and Colorists, PO Box 12215, Research Triangle Park, North Caroline 27709, USA.

All counts were measured as colony forming units per cm$^3$ (cfu/cm$^3$).

Washing of Fibres

Fabric samples made up of non-cellulosic fibres were washed using a standard method of the Home Laundry Consultative Council (HLCC), a United Kingdom group responsible for setting guidelines on washing of textile articles. Samples were taken at regular intervals and up to 25 washes were carried out.

The method used was 6A at 40° C. The details of the wash are as follows:

1. 6 minutes wash at 40° C.
2. 2 rinses of 3 minutes at 15° C.
3. 1 rinse of 2 minutes+spin of 1 minute
4. 1 rinse of 2 minutes+spin of 2 minutes The washing machine was a Wascator FOM 71. Each wash used 2 kg of sample, with 48 g of ECE Reference Detergent+12 g perborate bleach.

EXAMPLE 1 (E1)

Texchem™ 2700 is a modified DMDHEU resin supplied by Texchem Dyestuffs Ltd of Rochdale UK as an aqueous solution with 66% solids content and was used as supplied.

Condensol™ FC is a 50% aqueous solution of MgCl$_2$ and other components, and was used as supplied by BASF plc, Ludwigshafen, Germany.

Reputex™ 20 is a 20% aqueous solution of PHMB supplied by Avecia Ltd of Blackley, UK and was used as supplied.

A mixture was prepared of 100 g Texchem™ 2700, 30 g Condensol™ FC and 40 g Reputex™ 20 and made up to 1000 cm$^3$ with water, and charged to the trough of a laboratory pad/mangle. A piece of 100% polyester fabric, size 25 cm×25 cm was fed through the pad, and squeezed to give a pick-up of 50%. The fabric was then air dried, and heat cured at 160° C. for 3 minutes, rinsed in warm water and air dried.

EXAMPLE 2 (E2)

Baypret™ R is a modified DMDHEU resin supplied by Bayer AG of Leverkusen, Germany as an aqueous solution with 60% solids content and was used as supplied.

A mixture was prepared of 100 g Baypret™ R, 30 g Condensol™ FC and 40 g Reputex™ 20 and made up to 1000 cm$^3$ with water, and charged to the trough of a laboratory pad/mangle. A piece of 100% polyester fabric 25 cm×25 cm was fed through the pad, and squeezed to give a pick-up of 50%. The fabric was then air dried, heat cured at 160° C. for 3 minutes, rinsed in warm water and air dried.

COMPARATIVE EXAMPLE 1 (CE1)

Untreated 100% polyester fabric. This example is a control sample with no additional treatment.

COMPARATIVE EXAMPLE 2 (CE 2)

40 g Reputex™ 20 made up to 1000 cm$^3$ with water was charged to the trough of a laboratory pad/mangle. A piece of 100% polyester fabric, 25 cm×25 cm was fed through the pad, and squeezed to give a pick-up of 50%. The fabric was then air dried, heat cured at 160° C. for 3 minutes, rinsed in warm water and air dried. This example is a control sample with antimicrobial active agent but no self-crosslinkable resin or catalyst.

The fabric was washed up to 25 times at 40° C.

All of the fabrics were washed up to 25 times at 40° C., and the durability to washing was measured using the Eosin Y staining technique and the results are given below in Table 2:

TABLE 2

| Example | Unwashed | 1 wash | 10 washes | 25 washes |
|---|---|---|---|---|
| E1 | Strong pink stain | Medium pink stain | Medium pink stain | Medium pink stain |
| E2 | Strong pink stain | Medium pink stain | Medium pink stain | Medium pink stain |
| CE1 | No stain | No stain | No stain | No stain |
| CE2 | Strong pink stain | No stain | No stain | No stain |
| CE3 | No stain | No stain | No stain | No stain |
| CE4 | No stain | No stain | No stain | No stain |

Table 2 shows that the fabric itself, the self-crosslinkable resin and the catalyst do not stain pink with Eosin Y.

When the antimicrobial active agent was applied without any self-crosslinkable resin a pink stain was obtained. However after a single wash the stain was lost showing clearly that the antimicrobial active agent was not durable to washing.

The level of anti-bacterial activity was measured as described above and the results are given in Table 3 below:

TABLE 3

| | Unwashed | | 1 wash | | 10 washes | | 25 washes | |
|---|---|---|---|---|---|---|---|---|
| Example | Bacterial count Cfu/cm$^3$ | Log reduction v control | Bacterial count Cfu/cm$^3$ | Log reduction v control | Bacterial count Cfu/cm$^3$ | Log reduction v control | Bacterial count Cfu/cm$^3$ | Log reduction v control |
| E1 | <100 | 5.8 | <100 | 5.9 | <100 | 6.1 | <100 | 6.3 |
| E2 | <100 | 5.8 | <100 | 5.9 | <100 | 6.1 | <100 | 6.3 |
| CE1 | $5.9 \times 10^7$ | 0 | $6.7 \times 10^7$ | 0 | $1.1 \times 10^8$ | 0 | $2.0 \times 10^8$ | 0 |
| CE2 | <100 | 5.8 | $9.8 \times 10^7$ | 0 | $9.8 \times 10^7$ | 0 | $1.2 \times 10^8$ | 0 |
| CE3 | $6.7 \times 10^7$ | 0 | — | — | $6.7 \times 10^7$ | 0 | $8.6 \times 10^7$ | 0 |

COMPARATIVE EXAMPLE 3 (CE 3)

A mixture was prepared of 100 g Texchem™ 2700 and 30 g Condensol™ FC and made up to 1000 cm$^3$ with water and charged to the trough of a laboratory pad/mangle. A piece of 100% polyester fabric, 25 cm×25 cm was fed through the pad, and squeezed to give a pick-up of 50%. The fabric was then air dried, heat cured at 160° C. for 3 minutes, rinsed in warm water and air dried. This example is a control sample with self-crosslinkable resin and catalyst but no antimicrobial active agent.

COMPARATIVE EXAMPLE 4 (CE 4)

A mixture was prepared of 100 g Baypret™ R and 30 g Condensol™ FC and made up to 1000 cm$^3$ with water and charged to the trough of a laboratory pad/mangle. A piece of 100% polyester fabric, 25 cm×25 cm was fed through the pad, and squeezed to give a pick-up of 50%. The fabric was then air dried, heat cured at 160° C. for 3 minutes, rinsed in warm water and air dried. This example is a control sample with self-crosslinkable resin and catalyst but no antimicrobial active agent.

The invention claimed is:

1. A composition for inhibiting the growth of microorganisms on non-cellulosic fibres having a moisture regain of ≦5%, consisting of;
    i) 2 to 20 wt % of at least a self-crosslinkable resin;
    ii) 0.25 to 20 wt % of at least a catalyst selected from the group consisting of MgCl$_2$, ammonium chloride, ammonium sulphate, ammonium salt of boric acid, and combinations thereof;
    iii) 0.1 to 4 wt % of at least an antimicrobial active agent, reactive with the resin, said antimicrobial active agent being selected from the group consisting of biguanides, monoguanides, and combinations thereof;
    iv) 75 to 97 wt % of water;
    wherein i)+ii)+iii)+iv)=100%.

2. A composition according to claim 1 where the non-cellulosic fibres have an acid value ≦5 mmol/kg.

3. A composition according to claim 1 where the non-cellulosic fibres are selected from the group consisting of polyester, polyamide, polypropylene, polyurethane and cellulose acetate.

4. A composition according to claim 1 where the self-crosslinkable resin is an amino resin.

5. A composition according to claim 4 where the self-crosslinkable resin is a formaldehyde condensate with urea or melamine.

6. A composition according to claim 5 where the self-crosslinkable resin is selected from dimethyloldihydroxyethylene urea and dihydroxydimethylene urea.

7. A composition for inhibiting the growth of microorganisms on non-cellulosic fibres having an acid value of $\leqq 5$ mmol/kg, consisting of;
   i) 2 to 20 wt % of at least a self-crosslinkable resin;
   ii) 0.25 to 20 wt % of at least a catalyst selected from the group consisting of $MgCl_2$, ammonium chloride, ammonium sulphate, ammonium salt of boric acid, and combinations thereof;
   iii) 0.1 to 4 wt % of at least an antimicrobial active agent, reactive with the resin, said antimicrobial active agent being selected from the group consisting of biguanides, monoguanides, and combinations thereof;
   iv) 75 to 97 wt % of water;
   wherein i)+ii)+iii)+iv)=100%.

8. A composition according to claim 7 where the non-cellulosic fibres have a moisture regain of $\leqq 5\%$.

9. A method for inhibiting the growth of microorganisms on non-cellulosic fibres having a moisture regain of $\leqq 5\%$, comprising stages:
   A) contacting the fibres with a composition according to claim 1;
   B) optionally drying the fibres contacted with the composition; and
   C) curing the fibres contacted with the composition to effect crosslinking of the resin.

10. A method according to claim 9 where the non-cellulosic fibres have an acid value of $\leqq 5$ mmol/kg.

11. A method according to claim 9 where stage C) is carried out at temperatures in the range of from 100 to 180° C.

12. A method according to claim 9 where stage C) is carried out for a time in the range of from 30 seconds to 5 minutes.

13. A method for inhibiting the growth of microorganisms on non-cellulosic fibres having an acid value of $\leqq 5$ mmol/kg, comprising stages:
   A) contacting the fibres with a composition according to claim 1;
   B) optionally drying the fibres contacted with the composition; and
   C) curing the fibres contacted with the composition to effect crosslinking of the resin.

14. A method according to claim 13 where the non-cellulosic fibres have a moisture regain of $\leqq 5\%$.

15. Non-cellulosic fibres having a moisture regain of $\leqq 5\%$ treated with a composition according to claim 1.

16. Non-cellulosic fibres having an acid value of $\leqq 5$ mmol/kg treated with a composition according to claim 7.

* * * * *